United States Patent [19]

Möller et al.

[11] 4,077,776

[45] Mar. 7, 1978

[54] GAS AND GAS-CARRIED SUSPENDED MATTER INDICATOR TUBE HAVING FIXING ELEMENTS FOR REAGENT CARRIERS

[75] Inventors: Hans Möller; Bernd Mussmann, both of Lubeck, Germany

[73] Assignee: Dragerwerk Aktiengesellschaft, Germany

[21] Appl. No.: 802,434

[22] Filed: Jun. 1, 1977

[30] Foreign Application Priority Data

Jun. 18, 1976 Germany .............................. 2627315

[51] Int. Cl.² ...................... G01N 31/06; G01N 31/22
[52] U.S. Cl. ................................................. 23/254 R
[58] Field of Search ............ 23/254 R, 255 R, 232 R; 116/114 AM

[56] References Cited

U.S. PATENT DOCUMENTS

| 1,321,062 | 11/1919 | Lamb et al. | 23/254 R X |
| 2,908,555 | 10/1959 | Grosskopf | 23/254 R |
| 3,378,348 | 4/1968 | McConnaughey | 23/254 R |

*Primary Examiner*—Robert M. Reese
*Attorney, Agent, or Firm*—McGlew and Tuttle

[57] ABSTRACT

The gas or gas-carried suspended matter indicator tube includes a reagent therein for detecting gases or suspended matter in the gas which are passed through the tube. The tube is drawn down at each end and sealed. Each end of the tube or the portion of the tube at which the reagent ends, is retained by fixing elements, which comprise glass granules which are sintered.

5 Claims, 2 Drawing Figures

GAS AND GAS-CARRIED SUSPENDED MATTER INDICATOR TUBE HAVING FIXING ELEMENTS FOR REAGENT CARRIERS

FIELD AND BACKGROUND OF THE INVENTION

The present invention relates to gas and gas-carried suspended matter indicators and, in particular, to a new and useful indicator tube accommodating fixing elements for the reagent carriers.

DESCRIPTION OF THE PRIOR ART

In order to detect gases, suspended matter, or the like, in air or other gases, so-called indicator tubes are employed. A sample of air or other gas is drawn by suction through these indicator tubes with the aid of an air-conveying device. A carrier is received in the indicator tube, generally of granular structure, which comprises or is coated with a reagent for detecting certain components. The granular carriers must be held in place in the indicator tube, which is usually a glass tube, firmly, and in a shake-proof manner. Fixing elements are used for this purpose. The introduction of known fixing elements, particularly into a glass tube which is end-drawn to a tip prior to the filling, it painstaking.

Indicator tubes are known in which the fixing elements comprise glass wool stoppers. The manufacture of these glass wool stoppers, which must be of equal size and must have equal resistances to the gas flow therethrough, is complicated. In particular, their introduction into the closed end with the drawn-out tip is difficult. These operations can only be carried out manually.

A known indicator tube is provided with fixing means consisting of two elements. First, a fixing piece is inserted on which, in addition, a small plate, permeable to air is placed, which is made of an inert material. The fixing piece comprises a cone-shaped shell in the interior of which a cylindrical stub, having a passage opening, is formed. The material of the fixing piece is a resilient plastic. The cone-shaped shell must apply against the inside surface of the glass tube and, thereby, hold the fixing piece in place.

These known fixing means comprising a fixing piece and a small plate can be used only for the indication of gases to which they are resistant. The insertion of two individual elements is particularly difficult (German Utility Model No. 19 24 162).

Other known indicator tubes contain a filler in which the reagent carrier comprises plastic material which is breakable at normal temperatures of between −20° and +20° C. In order to hold the layers in place, fixing elements made of TEFLON or polyethylene are used. In view of the range of chemical resistance of these materials, the possibilities of application are limited (German Pat. No. 1,105,640).

SUMMARY OF THE INVENTION

The present invention is directed to a reduction of the variety of different fixing elements and to the elimination of the troublesome manipulation connected with their introduction into the empty indicator tubes.

To this end, and in accordance with the invention, the fixing elements are made of sintered glass granules. The advantages obtained with this solution are, primarily, that sintered fixing elements of glass granules, which may be made of any sort of glass, colored or colorless, have a high mechanical resistance. Further, by selecting the size of the glass granules, the resistance to flow therethrough can be determined prior to the sintering process. Additionally, the fixing elements are easy to handle, and no abrasion is to be expected.

In a development of the invention, it is provided to sinter the fixing elements directly in position within the end of the glass tube which has been drawn to a tip prior to the filling operation. With this provision, any subsequent insertion is avoided. The fixing element may be formed during the manufacture of the glass tube so as to fit the indicator tubes being formed.

In a preferred embodiment, the fixing elements have the shape of a ball or cylinder matching the inside diameter of the glass tube. Such fixing elements can be introduced mechanically into the glass tube end after it is drawn to a tip, prior to the filling of the glass tube with the reagent carrier.

After the reagent carrier has been filled in, they can be used as the respective upper fixing element, or, in multilayer indicator tubes, also as an intermediate fixing element. Their firm attachment to the inside surface of the glass tube may be obtained, for example, by means of an adhesive or by bracing.

It may be easily understood that the equally shaped and sized fixing elements can be introduced in a simple, mechanical and, thereby, economically advantageous manner.

Accordingly, it is an object of the invention to provide an indicator tube having a reagent carrier therein for indicating a gas or suspended matter within a gas, and which includes fixing elements comprising sintered glass granules arranged adjacent the reagent carriers.

A further object of the invention is to provide a method of forming a gas indicator tube which includes inserting a reagent carrier into the tube, applying glass granules into the tube to abut against the reagent carrier and drawing the ends of the tubes down and closing the tube.

Another object of the invention is to provide an indicator tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

DESCRIPTION OF THE PREFERRED EMBODIMENTS

Figures 1, 2:
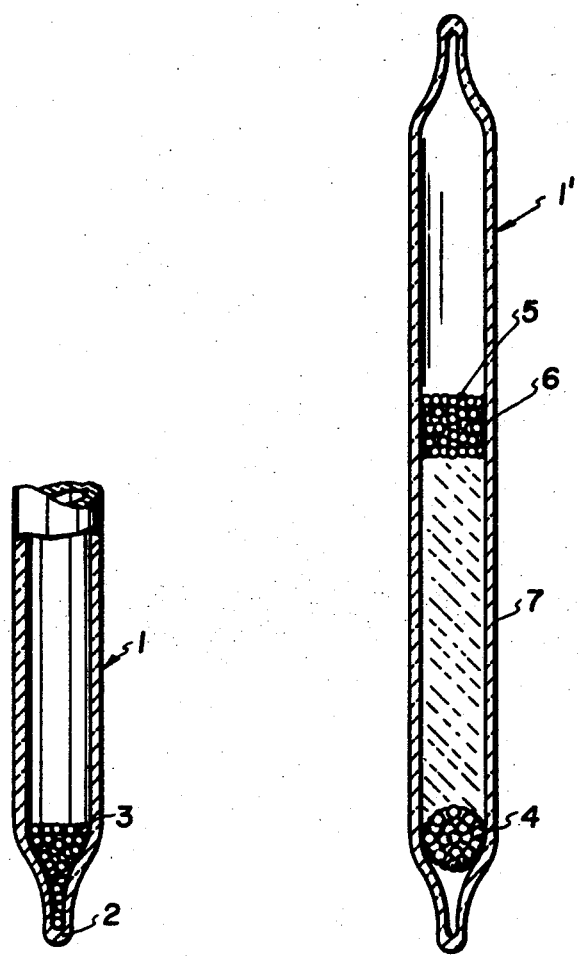
FIG. 1 is a partial sectional view of a non-filled glass tube with a fixing element sintered in place, in accordance with the invention.
FIG. 2 is a view similar to FIG. 1 of a finished indicator tube accommodating sintered fixing elements of different shape.

Referring to the drawing in particular, the invention embodied therein in FIG. 1, comprises an indicator tube, generally designated 1, which, in accordance with the method of the invention, is filled with a reaction material for indicating a gas composition or a suspension in a gas and then its end is closed by drawing it down to a tip 2 after glass granules are inserted in the tube 1, and these granules are either sintered simultaneously with the drawing down or prior thereto.

Glass tube 1, shown in FIG. 1, is shown as being closed on one of its ends by a drawn-out tip 2. A fixing element 3 of glass granules received therein is mechanically filled in and then sintered. Due to the size of the granules and the repeatedly uniform mechanical operation, an identical mechanical resistance and size of pores is ensured. Prior to using the indicator tube, as soon as the tip is broken away, the way is cleared for the gas to be tested to pass through the pores of the fixing element sintered in place.

FIG. 2 shows two embodiments of fixing elements as loose pieces arranged in a tube 1'. Element 4 has the shape of a ball, and element 5 has the shape of a cylinder. It is easily understood that such elements 4 and 5 of constantly uniform shape and size can be introduced mechanically by the filling machine (not shown). By avoiding manual work, the manufacture of the tubes is rendered more economical and secure.

The cylindrical fixing element 5 may be held in place on the inside surface of glass tube 7 by means of an adhesive 6.

While specific embodiments of the invention have been shown and described in detail to illustrate the application of the principles of the invention, it will be understood that the invention may be embodied otherwise without departing from such principles.

What is claimed is:

1. An indicator tube, comprising a glass tube having a reagent carrier therein for indicating a gas or a suspension in a gas and a fixing element for the reagent carrier comprising sintered glass granules.

2. An indicator tube, as claimed in claim 1, wherein said tube has an end drawn down to a tip and closed, said glass granules being arranged adjacent said tip and separating the reagent carrier from the tip.

3. An indicator tube, as claimed in claim 1, wherein said tube includes a tip formation adjacent one end and is closed at said one end, said granules being in the tube adjacent said end and being sintered in position therein.

4. An indicator tube, as claimed in claim 1, wherein said sintered glass granules are arranged in the form of a ball fitting the inside diameter of said glass tube.

5. An indicator tube, as claimed in claim 1, wherein said sintered glass granules are arranged in the form of a cylinder fitting the inside diameter of said glass tube.

* * * * *